US010323040B2

(12) United States Patent
Pruehs et al.

(10) Patent No.: US 10,323,040 B2
(45) Date of Patent: Jun. 18, 2019

(54) PROCESS FOR THE PREPARATION OF 5-FLUOROTRYPTOPHOL

(71) Applicant: Gruenenthal GmbH, Aachen (DE)

(72) Inventors: Stefan Pruehs, Neuss (DE); Olaf Schaefer, Stolberg (DE)

(73) Assignee: GRUENENTHAL GMBH, Aachen (DE)

( * ) Notice: Subject to any disclaimer, the term of this patent is extended or adjusted under 35 U.S.C. 154(b) by 45 days.

(21) Appl. No.: 15/248,553

(22) Filed: Aug. 26, 2016

(65) Prior Publication Data

US 2016/0362417 A1    Dec. 15, 2016

Related U.S. Application Data

(63) Continuation of application No. PCT/EP2015/000441, filed on Feb. 26, 2015.

(30) Foreign Application Priority Data

Feb. 27, 2014 (EP) .................................. 14000696.6

(51) Int. Cl.
*C07D 491/107* (2006.01)
*C07D 209/12* (2006.01)
*C07D 209/30* (2006.01)

(52) U.S. Cl.
CPC ....... *C07D 491/107* (2013.01); *C07D 209/12* (2013.01); *C07D 209/30* (2013.01)

(58) Field of Classification Search
None
See application file for complete search history.

(56) References Cited

U.S. PATENT DOCUMENTS

| | | |
|---|---|---|
| 2006/0166947 A1 | 7/2006 | Anderson et al. |
| 2009/0111842 A1 | 4/2009 | Merla et al. |
| 2010/0009986 A1 | 1/2010 | Zemolka et al. |
| 2010/0048554 A1 | 2/2010 | Schunk et al. |
| 2015/0322080 A1 | 11/2015 | Hinze et al. |
| 2015/0342929 A1 | 12/2015 | Linz et al. |

FOREIGN PATENT DOCUMENTS

| | | |
|---|---|---|
| WO | WO 03/099824 A1 | 12/2003 |
| WO | WO 2004/043967 A1 | 5/2004 |
| WO | WO 2007/124903 A1 | 11/2007 |
| WO | WO 2008/009415 A2 | 1/2008 |
| WO | WO 2008/040481 A1 | 4/2008 |
| WO | WO 2008/101659 A1 | 8/2008 |

OTHER PUBLICATIONS

International Search Report (PCT/ISA/210) issued in PCT Application No. PCT/EP2015/000441 dated Apr. 1, 2015 (Three (3) pages).
Written Opinion (PCT/ISA/237) issued in PCT Application No. PCT/EP2015/000441 dated Apr. 1, 2015 (Four (4) pages).
Demerson, C. A., et al., "Etodolic Acid and Related Compounds. Chemistry and Antiinflammatory Actions of Some Potent Di- and Trisubstituted 1,3,4,9-Tetrahydropyrano [3,4-b] indole-1-acetic Acids", Journal of Medical Chemistry, 1976, vol. 19, No. 3, pp. 391-395 (Five (5) pages).
Campos, K. R., et al., "A General Synthesis of Substituted Indoles from Cyclic Enol Ethers and Enol Lactones", Organic Letters, Jan. 1, 2004, vol. 6, No. 1, pp. 79-82, XP055123611 (Four (4) pages).
Soubhye, J., et al., "Structure-Based Design, Synthesis, and Pharmacological Evaluation of 3-(Aminoalkyl)-5-fluoroindoles as Myeloperoxidase Inhibitors", Journal of Medical Chemistry, Dec. 23, 2010, vol. 53, No. 24, pp. 8747-8759, XP055039524 (Thirteen (13) pages).
Singh, P. R., et al., "An Expeditious and Environmentally Benign Methodology for the Synthesis of Substituted Indoles from Cyclic Enol Ethers and Enol Lactones", Tetrahedron Letters, May 12, 2008, vol. 49, No. 20, pp. 3335-3340, XP022613651 (Six (6) pages).
McKittrick, B., et al., "Syhthetic Entries to 6-Fluoro-7-substituted Indole Derivatives", J. Hetereocyclic Chem, Nov.-Dec. 1990, vol. 27, 2151-2163 (Thirteen (13) pages).
Mewshaw, R. E., et al., "Studies toward the Discovery of the Next Generation of Antidepressants, 3 Dual 5-HT1A and Serotonin Transporter Affinity within a class of N-Aryloxyethylindolylalkylamines", J. Med. Chem. 2004, vol. 47, No. 15, pp. 3823-3842 (Twenty (20) pages).
Lu, Y., et al., "Novel Synthesis Technology of 7-Ethyltryptophol", Journal of Chemical Engineering of Chinese Universities, with English translation, Feb. 2010, vol. 24, No. 1, pp. 127-131, XP009178567 (Thirteen (13) pages).
Soubhye, J., et al., "Design, Synthesis, and Structure-Activity Relationship Studies of Novel 3-Alkylindole Derivatives as Selective and Highly Potent Myeloperoxidase Inhibitors", with supporting information, Journal of Medical Chemistry, May 23, 2013, vol. 56, No. 10, pp. 3943-3958, XP055178742 (Two-hundred and one (201) pages).
Wang, S., et al., "Synthesis and Evaluation of Novel 2, 3-Dihydrobenzo [ b ] [1,4] dioxin- and Indolealkylamine Derivatives as Potential Antidepressants", Arch. Pharm. Chem. Life Sci. 2014, vol. 347, pp. 32-41, DOI:10.1002/ardp.201300238 (Ten (10) pages).

*Primary Examiner* — Po-Chih Chen
(74) *Attorney, Agent, or Firm* — Norris McLaughlin PA

(57) ABSTRACT

The present invention relates to a process for the preparation of 5-fluorotryptophol as well as a process for the preparation of (1r,4r)-6'-fluoro-N,N-dimethyl-4-phenyl-4',9'-dihydro-3'H-spiro[cyclohexane-1,1'-pyrano-[3,4b]-indol]-4-amine using the 5-fluorotryptophol obtained by said first process. The process according to the invention provides 5-fluorotryptophol in improved yield and purity without the need for chromatographic purification of the product.

20 Claims, 3 Drawing Sheets

Figure 1B:
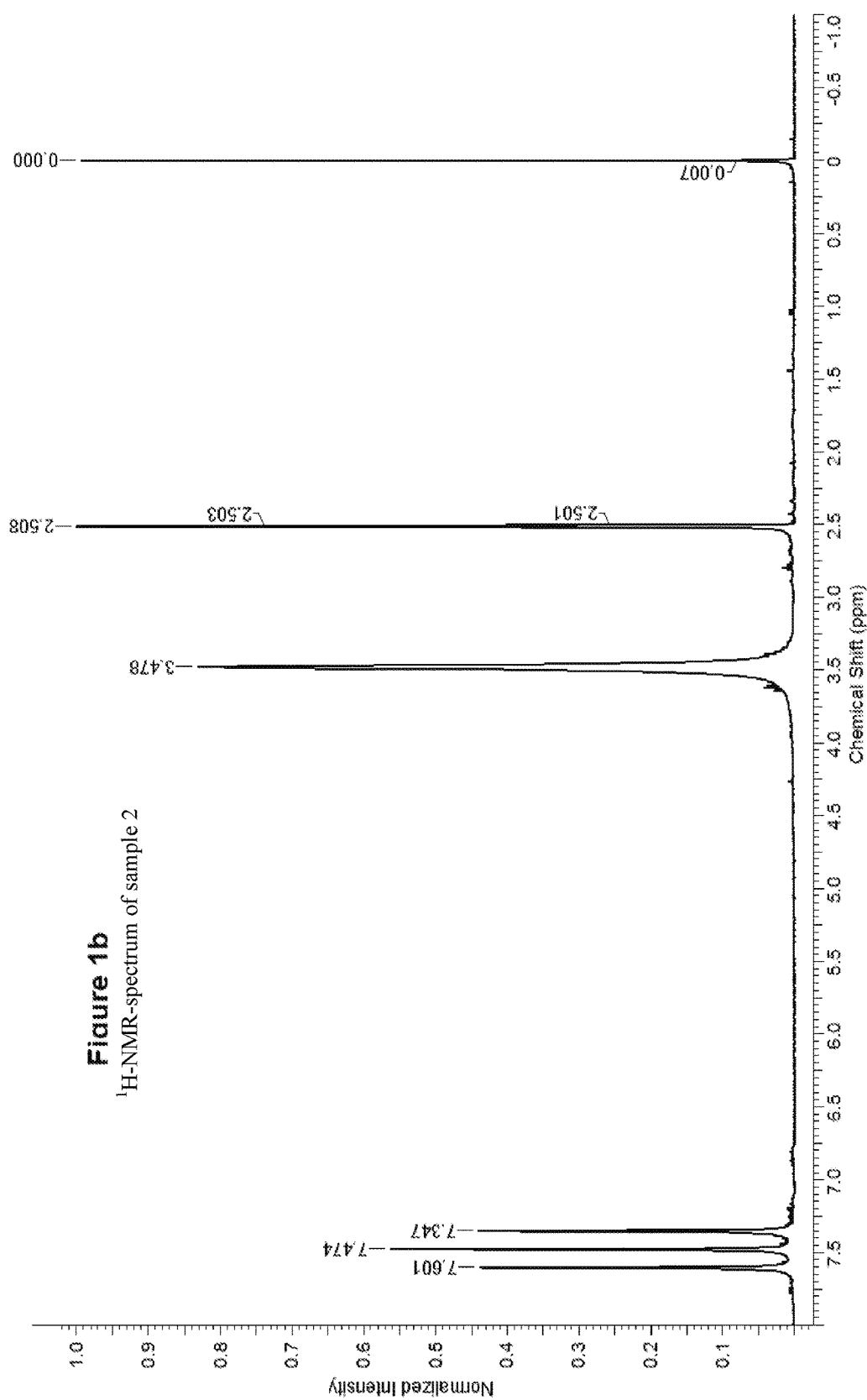

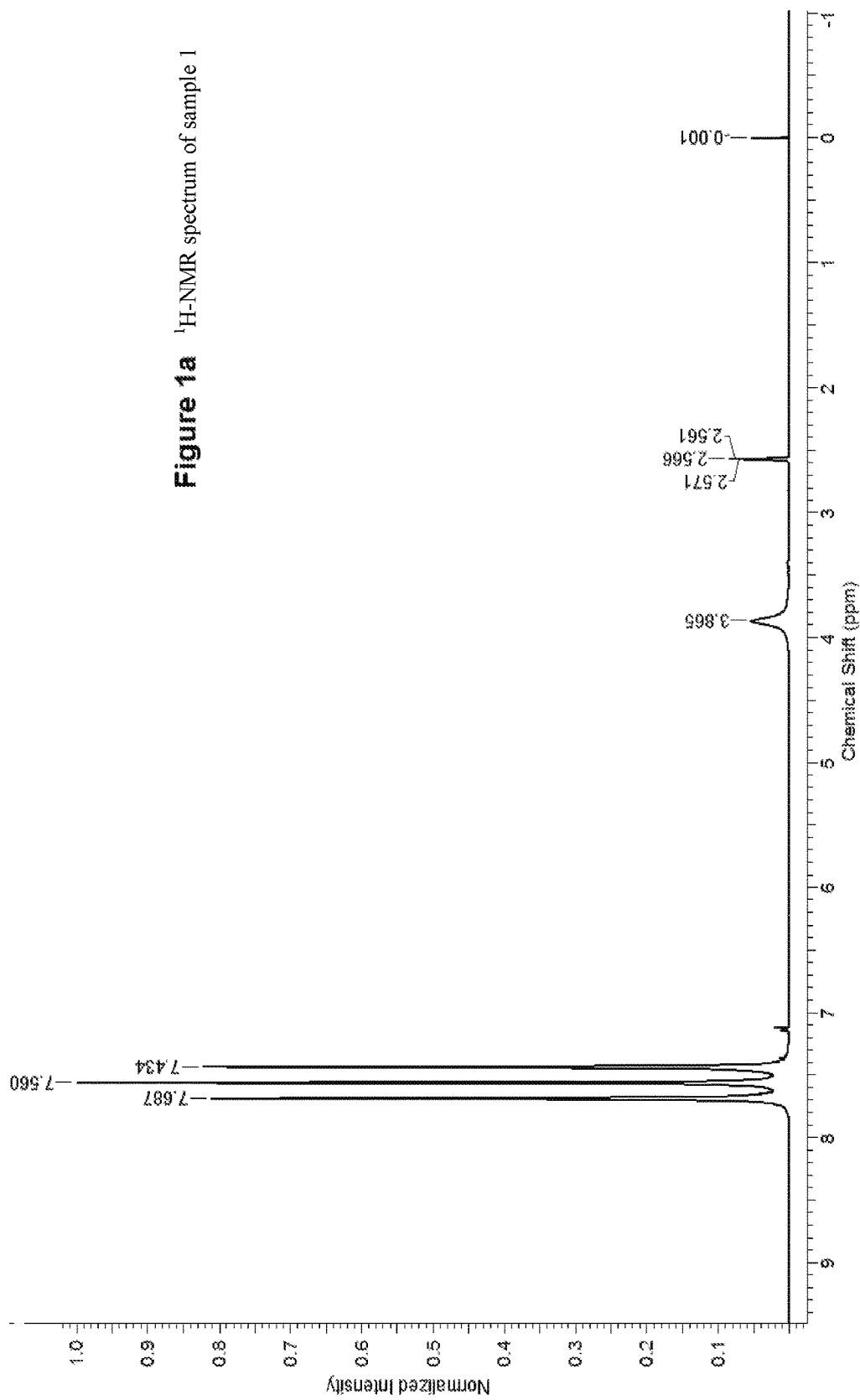
Figure 1a ¹H-NMR spectrum of sample 1

¹H-NMR-spectrum of sample 2

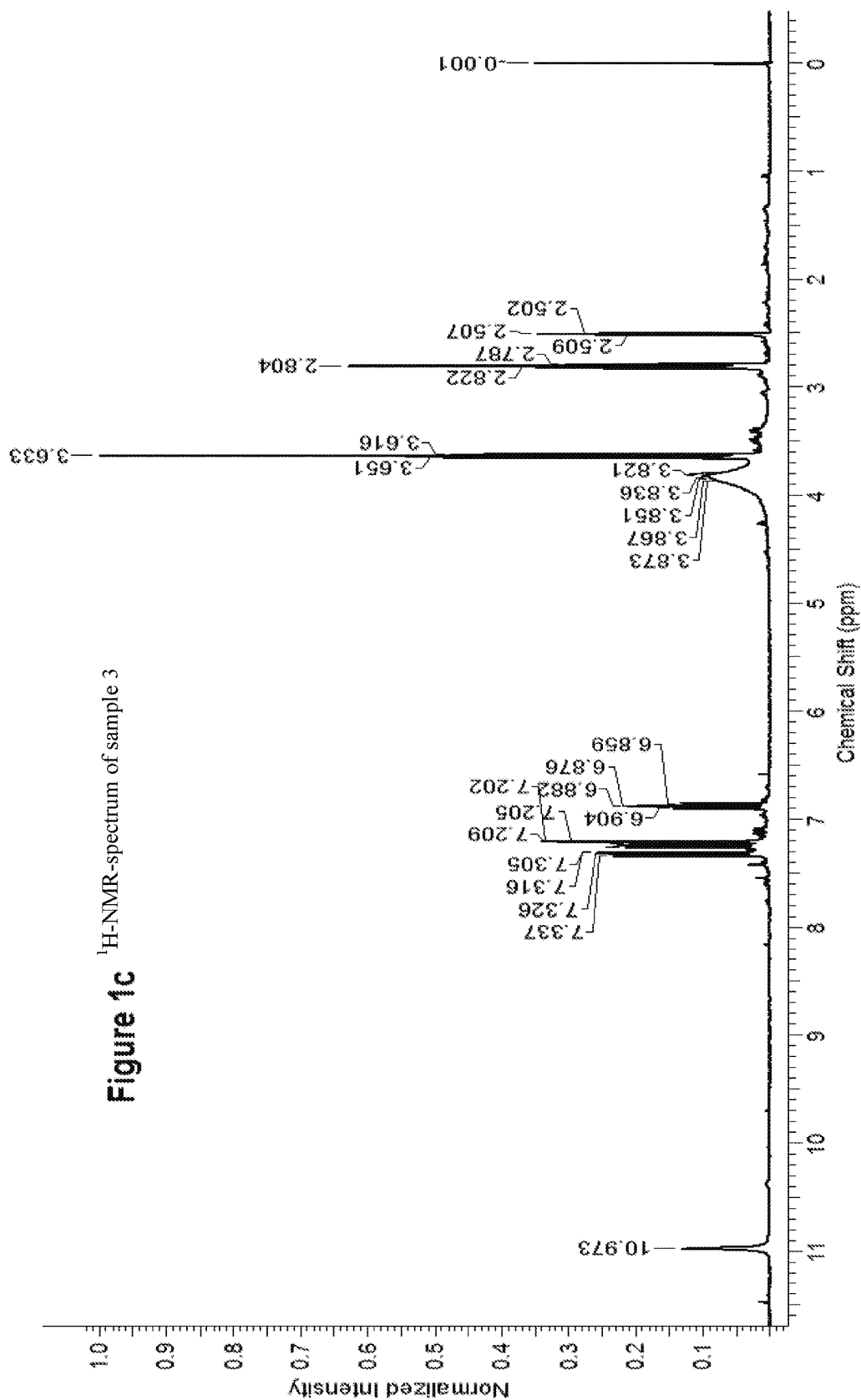
Figure 1c  ¹H-NMR-spectrum of sample 3

PROCESS FOR THE PREPARATION OF 5-FLUOROTRYPTOPHOL

This application is a continuation of international patent application no. PCT/EP2015/000441, filed Feb. 26, 2015 designating the United States of America, and published in English as WO 2015/128088 on Sep. 3, 2015, the entire disclosure of which is incorporated herein by reference. Priority is claimed based on EP 14 000 696.6, filed on Feb. 27, 2014.

The invention relates to a process for the preparation of 5-fluorotryptophol. In another aspect, the present invention relates to a process for the preparation of (1r,4r)-6'-fluoro-N,N-dimethyl-4-phenyl-4',9'-dihydro-3'H-spiro[cyclohexane-1,1'-pyrano-[3,4b]-indol]-4-amine or physiologically acceptable acid addition salts thereof.

Tryptophol derivatives are known as building blocks for the synthesis of pharmaceutically active substances. 5-Fluorotryptophol [2-(5-Fluor-1H-indol-3-yl)-ethanol] is for instance described as a building block in the synthesis of substituted spirocyclohexane compounds which are inter alia known from WO 2004/043967 and WO 2008/040481, e.g. (1r,4r)-6'-fluoro-N,N-dimethyl-4-phenyl-4',9'-dihydro-3'H-spiro[cyclohexane-1,1'-pyrano-[3,4b]-indol]-4-amine and (1r,4r)-6'-fluoro-N-methyl-4-phenyl-4',9'-dihydro-3'H-spiro[cyclohexane-1,1'-pyrano-[3,4b]-indol]-4-amine.
These compounds act as mixed NOP-/µ-opioid-receptor agonists and are of special interest for the treatment of pain such as acute, visceral, neuropathic, cancer and chronic pain.

Several synthetic routes to tryptophols are known in the art. It is for instance known to synthesize tryptophols via multi-step syntheses using isatines as starting materials. This route requires the use of strong reducing agents such as LiAlH$_4$, which makes it difficult to upscale these reactions from laboratory to technical scale. Such syntheses are for instance described by C. A. Demerson et al in *J. Med. Chem.* 1976, 19, 391-395. See also WO2008009415, WO2007/124903, WO 2008101659, and US 2006/0166947A1.

Another route to synthesize tryptophols uses a Fischer-Indole reaction for the cyclization of aryl hydrazines and aldehydes in the presence of acids such as strong mineral acids, e.g. H$_2$SO$_4$, immobilized heterogeneous Brønsted acidic catalysts such as Montmorillonite K10 or Lewis acids such as ZnCl$_2$. See for instance K. R. Campos et al, *Org. Lett.*, Vol 6, No. 1, 2004, 79-82; J. Soubhye et al, *J. Med. Chem.* 2010, 53, 8747-8759; P. K. Singh et al. Tetrahedron Letters 49 (2008) 3335-3340, WO 03/099824 A1, B. McKittrick et al., *J. Heterocyclic Chem,* 27, 2151 (1990), US 2006/0166947 and R. E. Mewshaw et al., *J. Med. Chem.* 2004, 47, 3823-3842. These reactions, in so far as they are explicitly described, are carried out in a homogeneous aqueous solvent system using a water-miscible organic co-solvent together with water. Co-solvents used are for instance THF, dimethylacetamide, acetonitrile, DMF, or dioxane. According to P. K. Singh et al. (see above) in purely aqueous systems and using Montmorillonite K10 as a heterogeneous catalyst the tryptophol reaction product and enol ether starting material form a highly concentrated organic layer. This is said to lead to the formation of unwanted by-products, and it is suggested to use certain polar, water-miscible co-solvents in order to avoid the formation of a heterogeneous solvent system and to thereby reduce the formation of unwanted by-products.

In all of the above described synthetic routes the tryptophols, if isolated at all, are purified via chromatographic methods such as column or flash chromatography which makes these methods unsuitable for use on a larger, technical scale.

One of the problems encountered when using the Fischer-Indole cyclization reaction to synthesize tryptopholes is the formation of unwanted by-products. One side-reaction that is observed in these reactions leads to the formation of a triol compound via reaction of the initially formed tryptophol with unreacted enol ether such as dihydropyrane or dihydrofurane, e.g.:

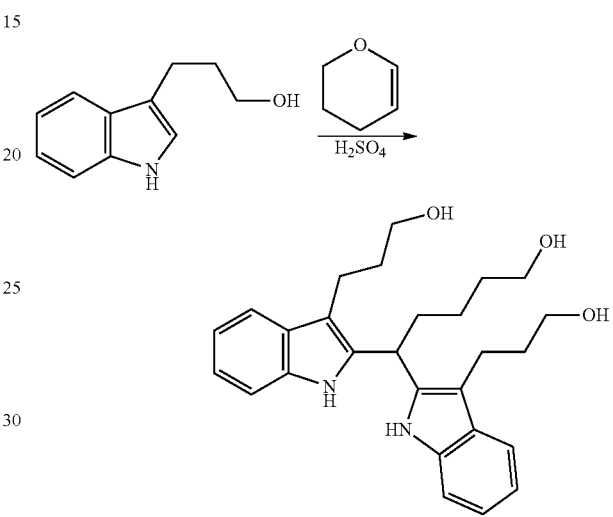

For the synthesis of 7-ethyltryptophol, an intermediate in the preparation of the non-steroidal anti-inflammatory drug etodolac, a two-step Fischer-Indole reaction synthesis using 2,3-dihydrofuran and ethylphenyl hydrazine-HCl is known, in which in a first step the corresponding phenylhydrazone is formed which is then further reacted to give the product. This product is isolated after several purification steps via crystallization from cyclohexane. It is described that an improved selectivity and an increased yield can be achieved by means of the following measures: a) control of pH-value during the initial formation of the hydrazone (weakly acidic), b) addition of NaHSO$_3$ at the end of the hydrazone formation to remove excess 4-hydroxybutyraldehyde, c) slow addition of H$_2$SO$_4$ during the Fischer cyclization step, d) diluting the Fischer reaction system with ethanol and toluene to reduce occurrence of intermolecular reactions by in-situ extraction of the formed product from the aqueous phase, and e) adjustment of the pH-value after the reaction to a pH-value about 8. The reaction is said to provide a crude product of 7-ethyltryptophol which has a purity of above 80% and to yield the purified product in a yield of above 60%. (See Y. Lü et al., Journal of Chemical Engineering of Chinese Universities, No. 1, Vol. 24, 2010, p 127 to 131.)

The synthesis of 5-fluorotryptophol via a Fischer-Indole reaction is described by P. K. Singh et al. (see above), K. R. Campos et al. (see above) and J. Soubhye et al. (see above). A typical reaction scheme, e.g. as described by K. R. Campos, is shown below:

Reaction scheme 1: Acid catalyzed Fisher-Indole cyclization of phenylhydrazines and enol ethers to tryptopholes.

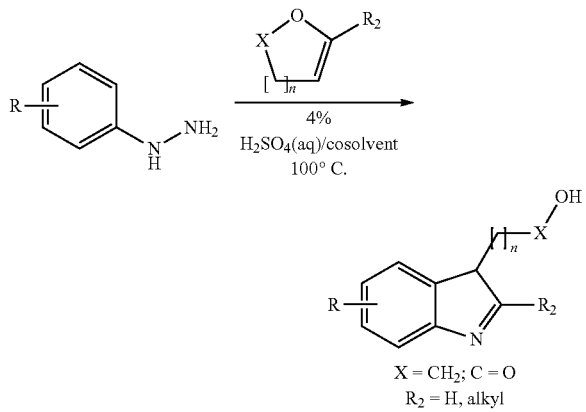

$X = CH_2; C = O$
$R_2 = H$, alkyl

All of these procedures use N,N-dimethylacetamide (DMA or DMAC) as a water-miscible organic co-solvent during the Fischer-Indole cyclization reaction. It is described that the reaction product is isolated from the crude product via chromatography.

5-Flurotryptophol has a relatively low melting point of about 60° C. Consequently, the ease of crystallisation of the compound is strongly dependent on its purity. Residual by-products and solvents hinder the crystallization and often 5-fluorotryptophol can only be isolated as an oily, highly viscous fluid. This, too, creates problems when trying to upscale the synthesis to a technical scale, because oily fluids are much more difficult to handle in technical scale processes than solid crystalline products. DMAC, which in the above mentioned citations is described as the water-miscible co-solvent of choice for the syntheses of 5-fluorotryptophol, is difficult to remove after the reaction and considerable amounts of residual solvent are found in the product if DMAC is for instance removed solely via distillation instead of removal during purification of the crude product via chromatography. Additionally, DMAC is toxic and environmentally hazardous and should therefore be avoided in commercial syntheses of pharmaceuticals. Due to its inherent toxicity only a very small amount of residual DMAC can be tolerated in pharmaceutical products and its removal from the active agent or the intermediate products used during its synthesis requires additional costly and time-consuming purification steps.

Consequently, there remains the need for a synthesis of 5-fluorotryptophol that is simple, cost-effective, which can be carried out in the scale of kilograms and which provides a product in relatively high purity and in a sufficient yield.

It is therefore the object of the present invention to provide a synthesis that at least partially overcomes the drawbacks of prior art syntheses. This object is achieved via the invention as defined herein.

The present invention provides a process based on a Fischer-Indole cyclization reaction that allows a one-step synthesis for 5-fluorotryptophol that can be carried out in the scale of kilograms. It has been surprisingly found that the process according to the invention yields 5-fluorotryptophol in relatively high purity, which can be isolated without the use of chromatographic methods via simple precipitation/crystallization. Furthermore, it has been surprisingly found that according to the process of the present invention removal of excess aldehyde from the reaction medium prior to the [3+3] cyclization of the Fischer-Indole reaction is not necessary. Furthermore, with the process according to the present invention, the use of solvents considered hazardous to health and environment can be avoided.

In a further aspect the present invention provides a process for the preparation of (1r,4r)-6'-fluoro-N,N-dimethyl-4-phenyl-4',9'-dihydro-3'H-spiro[cyclohexane-1,1'-pyrano-[3,4b]-indol]-4-amine using the 5-fluorotryptophol obtained via the process according to the first aspect of the invention.

The inventive process for preparing 5-fluorotryptophol comprises the steps of a.) providing a mixture comprising 4-fluorophenyl-hydrazine, an activation reagent, water and at least one aprotic organic solvent selected from the group consisting of tetrahydrofuran, 2-methyltetrahydrofuran and isopropyl acetate;

b) adding to the mixture a solution of at the most about 1.1 equivalents of 2,3-dihydrofuran in at least one aprotic organic solvent selected from the group consisting of tetrahydrofuran, 2-methyltetrahydrofuran and isopropyl acetate to react with the 4-fluorophenylhydrazine to give 5-fluorotryptophol, wherein the aprotic solvent and water provided in steps a) and b) are provided in a ratio relative to each other such that a heterogeneous reaction mixture comprising a liquid organic and a liquid aqueous phase is formed either before or during addition step b);

c) separating the organic from the aqueous phase;

d) contacting the organic phase with an aqueous solution of at least one inorganic salt to form a heterogeneous mixture comprising a liquid organic phase and a liquid aqueous phase;

e) separating the organic phase from the aqueous phase of the heterogeneous mixture; and f) isolating 5-fluorotryptophol from the organic phase via a precipitation step.

It has been surprisingly found that when carrying out the Fischer-Indole type reaction of 4-fluorophenylhydrazine, 2,3-dihydrofuran and the activation reagent in an heterogeneous reaction medium as described above, the occurrence of by-products is significantly reduced, which subsequently enables the isolation of high yields of crystalline 5-fluorotryptophol with a comparably high purity from the reaction mixture without the use of expensive chromatographic methods or the use of environmentally hazardous and toxic solvents such as DMAC.

In embodiments of the process according to the present invention, the mixture formed in step a) is a heterogeneous mixture comprising a liquid organic phase and a liquid aqueous phase.

The terms "aqueous liquid phase" and "organic liquid phase" as used herein to describe the properties of the heterogeneous reaction medium and any other heterogeneous mixture formed during the process are to be understood in the sense that an "aqueous liquid phase" is a liquid phase in which the primary solvent is water, but additional solvents, especially organic solvents may also be dissolved in the aqueous phase. Vice versa, an "organic liquid phase" is a phase in which the primary solvent is an organic solvent, but some water may also be dissolved in the organic phase. The person skilled in the art is aware that when an organic phase comprising an organic solvent is brought into contact with water, water will to some degree dissolve in the organic solvent and the organic solvent will to some degree dissolve into the water until the state of phase equilibrium is reached, which is governed by the respective solubility of each of the solvents in each other. In this respect, the term "water-miscible" organic solvent is used to describe such solvents which are described in the literature as soluble in water at any ratio, such as acetonitrile, DMF, DMAC, dioxane and THF. Organic solvents which form homogenous mixtures with water only within specific ratios of organic solvent and water are herein described as partially water-miscible or water-immiscible, respectively.

Contrary to the teaching in the above cited prior art processes for the preparation of 5-fluorotryptophol, in all of which the Fischer-Indole cyclization is carried out in a reaction medium comprising a single liquid phase, in the process according to the present invention the Fischer-Indole cyclization is carried out in such a way that the reaction takes place in heterogeneous reaction medium either directly from the start of addition step b) or that such a heterogeneous reaction medium is formed during the course of the addition of the solution comprising the 2,3-dihydrofuran. The heterogeneous reaction medium comprises a liquid aqueous phase and a liquid organic phase wherein the organic phase comprises at least one aprotic organic solvent selected from the group consisting of tetrahydrofuran, 2-methyltetrahydrofuran and isopropyl acetate. The organic phase may also comprise mixtures of one or more of the above listed aprotic solvents. Without wanting to be bound by theory it is believed that in this reaction medium, the 5-fluorotryptophol formed in the Fischer-Indole cyclization in the aqueous phase is quickly removed into the organic phase and therefore no longer available to undergo side-reactions with activated 2,3-dihydrofuran present in the aqueous phase. Additionally, it is believed that the respective solubilities of the organic solvent in water and vice versa provides conditions in both liquid phases of the heterogeneous reaction medium for the reactants, which result in a distribution equilibrium of the respective reactants in both phases which increases the selectivity of the reaction with regard of the formation of the targeted reaction product, i.e. 5-fluorotryptophol. Consequently, contrary to the prior art processes for the preparation of 5-fluorotryptophol, which try to avoid the presence of a heterogeneous reaction medium by using highly water miscible polar organic solvents such as DMAC as co-solvents together with water in quantities sufficient to form a single homogeneous fluid phase, the process according to the present invention uses a heterogeneous reaction medium to control the occurrence of unwanted by-products. It was found that when using non-polar, water-immiscible organic aprotic solvents such as toluene or benzene, alkanes such as pentane, hexane, heptane or cyclohexane, and halogenated alkanes such as dichloroethane, unwanted by-products are formed in an extent which makes it impossible to isolate the reaction product in crystalline form without prior purification via chromatographic methods. Again without wanting to be bound by theory, it is believed that when using such water-immiscible aprotic organic solvents the solubility of 5-fluorotryptophol in these organic solvents is not high enough to effectively remove 5-fluorotryptophol out of the aqueous phase. With other polar, partially water-miscible or water-miscible solvents such as ethanol, n-propanol, isopropanol, 2-methyl-1-propanol, n-butanol, acetic acid, or dioxane it was either not possible to form a heterogeneous reaction mixture and/or by-products were formed during the reaction in an amount which prohibited the isolation of 5-fluorotryptophol via simple precipitation/crystallization. Again without wanting to be bound by theory, it is believed that for these solvents, the distribution of reactants, including the activation agent, water and the aprotic solvent in the respective phases of the reaction medium does not enable a reaction sufficiently selective to yield the targeted 5-fluorotryptophol in a sufficient purity to enable its easy isolation via precipitation/crystallization. Similarly, the use of solvents such as n-butyl acetate, isobutyl acetate, tert-butyl acetate and methyl tert-butyl-ether did not give satisfactory results. It was surprisingly found that under the reaction conditions required for the Fischer-Indole cyclization, isopropyl acetate exhibited sufficient chemical stability and did not undergo de-esterification whereas ethyl acetate and tert-butyl acetate were prone to such a reaction, disqualifying these solvents already for this reason from use in the process according to the invention.

Additionally, it was found that when the reaction is carried out as described by Y. Lü et al (see above) for the synthesis of 7-ethyltryptophol, i.e. in a heterogeneous reaction medium comprising water, ethanol, and toluene as solvents, the reaction also lacks selectivity and facile isolation of 5-fluorotryptophol was not possible. Surprisingly, it was found that tetrahydrofuran, which is described in the literature as a water-miscible solvent, can also be used in the process according to the present invention because its water-miscibility is influenced by the presence of the reactants in the reaction medium in such a manner, that a heterogeneous reaction medium comprising an aqueous liquid phase and an organic liquid phase can be formed. Furthermore, it was found that by using the above mentioned solvents, all of which have a boiling point at ambient pressure well below that of DMAC, any residual solvent attached to the raw product can be relatively easily removed, e.g. via drying at reduced pressure and/or elevated temperature. This is especially helpful when 5-fluorotryptophol is to be isolated and/or purified via precipitation/crystallization.

Additionally, it was found that the occurrence of by-products is reduced by limiting the quantity of 2,3-dihydrofuran relative to 4-fluorophenylhydrazine to 1.1 equivalents. Again, without wanting to be bound by theory, it is believed that at higher relative quantities of 2,3-dihydrofuran, the reaction rate of the side reactions of 5-fluorotryptophol with 2,3-dihydrofuran is increased to an extent detrimental to the selectivity of the reaction and the thus formed quantities of by-products make it very difficult to subsequently isolate the product in sufficient purity. Preferably, the theoretically required relative amounts of each of the two reactants are used in the reaction, i.e. equimolar amounts of 4-fluorophenylhydrazine and 2,3-dihydrofuran. If 4-fluorophenylhydrazine is used in an excess relative to 2,3-dihydrofuran, it is preferred not use it in a ratio of below 0.9 equivalent relative to 4-fluorophenylhydrazine, as obviously the yield with respect to the more expensive reagent 4-fluorophenylhydrazine hydrochloride will be significantly decreased. Consequently, in further embodiments of the process according to the invention the ratio of 2,3-dihydrofuran relative to 4-fluorohydrazine hydrochloride is selected to be in the range of about 0.9 to 1.1 equivalents.

The isolation and purification of an organic reaction product is often carried out via solvent extraction, e.g. addition of a liquid aqueous phase to a liquid organic phase containing the raw product to form an finely dispersed heterogeneous mixture and subsequent phase separation of the mixture into a liquid aqueous and a liquid organic phase, whereby the product is enriched in one of the two phases, which is then isolated from the other and further worked with. Prerequisite for this purification step is that the mixture that is formed can be quickly separated again and does not form a stable emulsion. This is of special importance for large/technical scale processes as the time required for phase separations is known to increase with the batch size. It was surprisingly found that the raw product can be efficiently isolated and purified by extraction of the organic phase isolated from the reaction medium and containing the target compound when using an aqueous solution of at least one inorganic salt to wash said organic phase. The extraction using the aqueous salt solution removes a large amount of organic by-products into the aqueous phase but hardly any product. Additionally, it was found that the finely dispersed heterogeneous mixture formed in the washing step quickly separates again when using an aqueous solution of at least one inorganic salt to wash the organic phase, but not when using pure water as the aqueous phase in the initial washing step. Water can be used as a washing liquid in subsequent washings, if required. Unlike when using DMAC in the reaction medium as described in the prior art, removal of residual organic solvent from the raw product is easily achieved, which allows a reduction in the number of washing steps required for the removal of the co-solvent, thereby reducing the amount of waste material generated in the synthesis and reducing the time required for the process, both of which contribute to further cost reduction of the process.

The person skilled in the art is aware that the Fischer-Indole cyclization reaction used in the present invention to form the 5-fluorotryptophol is a reaction described in the literature as the reaction of a hydrazine with an aldehyde under formation of a hydrazone and subsequent [3+3]-rearrangement. It is therefore clear to the person skilled in the art that a) the 2,3-dihydrofuran used a reagent in the reaction represents a protected aldehyde that has to be activated via hydrolysis (see reaction scheme 2 below) in order to react with the 4-fluorophenylhydrazine and that b) such hydrolysis needs an activation reagent.

Reaction scheme 2: Activation of 2,3-dihydrofurane

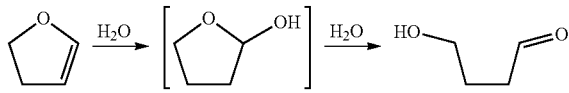

Such activation agents can for instance be organic or inorganic Brønsted acids, i.e. organic or inorganic protic acids, heterogeneous Brønsted acid catalysts or inorganic Lewis acids or mixtures thereof.

In one embodiment of the process according to the invention, the activation reagent is at least one organic or inorganic protic acid or a heterogeneous Brønsted acid catalyst.

In yet another embodiment of the inventive process, the activation reagent is, relative to 4-fluorophenylhydrazine, an at least equimolar amount of an organic or inorganic protic acid that has a pKa-value in the range of −6.5 to +10. Preferably the acid is selected from the group consisting of $H_2SO_4$, HCl, $NH_4HSO_4$, $(NH_4)_2SO_4$, acetic acid, $NH_4Cl$, $H_3PO_4$, $(NH_4)H_2PO_4$, $HClO_4$ or $(NH_4)ClO_4$. As the activation reagent, mixtures of these acids can be used as well. In a further embodiment of the inventive process, the activation reagent is selected from the group consisting of HCl, $H_2SO_4$, $H_3PO_4$, acetic acid and $NH_4Cl$ or mixture thereof. In a further embodiment, the activation reagent is HCl. In another embodiment, the activation reagent is $H_2SO_4$. It has been found that when using HCl or $H_2SO_4$ as the activation reagent, the reaction time required for completion of the Fischer-Indole cyclization can be minimized, especially, when said acids are used in an excess relative to the quantity of 4-fluorophenylhydrazine, which itself acts as a Brønsted base. If weaker acids are used as the activation reagent, the reaction time required for completion of the reaction at a given reaction temperature is found to be longer, but selectivity of the reaction might be increased compared to the use of the stronger acids. In further embodiments of the invention, the acid is selected from $NH_4Cl$, $NH_4HSO_4$ and $(NH_4)_2SO_4$. Depending on the activation reagent, batch-size and the reaction temperature used for the Fischer-Indole cyclization, the reaction time usually lies in the range of 2 to 48 h. For economic reasons it is of course preferred to use reaction conditions, which allow for relatively short reaction times, e.g. in the range of 2 to 24 h.

In a further embodiment of the invention, the activation reagent is at least one organic or inorganic protic acid, wherein the protic acid or acids are present in the reaction medium in an amount in excess of at least one equivalent relative to the amount of 4-fluorophenylhydrazine. In another embodiment of the inventive process, the activation reagent is a protic acid, wherein the protic acid is provided in the reaction medium in the form of its addition salt with 4-fluorophenylhydrazine. Consequently, in yet further embodiments of the inventive process, the activation reagent is HCl or $H_2SO_4$, these can be provided in the reaction medium by adding the salt 4-fluorophenylhydrazine hydrochloride or an addition salt of $H_2SO_4$ with 4-fluorophenylhydrazine to the reaction mixture. In the case that the activation reagent is added to the reaction medium in the form of its addition salt with 4-fluorophenylhydrazine, it is preferred to add an additional amount of activation agent to the reaction mixture so that the activation agent is present in an excess relative to the amount of 4-fluorophenylhydrazine. If for instance 4-fluorophenyl-hydrazine hydrochloride is used in the reaction medium, additional HCl or another activation agent can be added to the reaction medium, i.e. an additional amount of a protic organic or inorganic acid, e.g. $H_2SO_4$, $NH_4HSO_4$, $(NH_4)_2SO_4$, acetic acid, $NH_4Cl$, $H_3PO_4$, $(NH_4)H_2PO_4$, $HClO_4$ or $(NH_4)ClO_4$. In further embodiments of the inventive process, the amount of the additional protic acid is selected to be in the range of 0.1 to 2, specifically 0.5 to 1.5, and even more specifically 1.0 molar equivalent relative to the amount of 4-fluorophenylhydrazine.

4-fluorophenylhydrazine is commercially usually available in the form of its addition salt with HCl, i.e. as 4-fluorophenylhydrazine hydrochloride, making this the first choice for use in the inventive process. If a different addition salt is to be used by conversion of 4-fluorophenylhydrazine hydrochloride into its free base, e.g. via neutralization with aqueous NaOH solution, and subsequent addition of a protic acid to generate the addition salt, care must be taken to insure that a sufficient amount of the protic acid is added to compensate for the presence of any residual NaOH which could neutralize part of the protic acid. As a result less than an equimolar amount of activation agent would be present in the converted product. This would affect the subsequent cyclization reaction in a detrimental manner, reducing the rate of the reaction to a degree that would not allow for facile isolation of 5-fluorotryptophol via precipitation/crystallization.

In a further embodiment of the inventive process, the activation agent is present in the heterogeneous reaction media as a combination of an acid-addition salt of 4-fluorophenylhydrazine with a first acid, such as HCl or $H_2SO_4$, and a second, weaker acid selected from $NH_4Cl$, $NH_4HSO_4$ or $(NH_4)_2SO_4$ It has been found that compared to the use of an acid-addition salt alone, the additional presence of the second weaker acid in the reaction medium during the Fischer-Indole cyclization further accelerates the reaction and generates a pH-value in the aqueous phase of the reaction medium in the range of pH<7, preferably in the range of a pH<4. The use of the second, weaker protic acid in addition to the acid present in the reaction medium as part of the acid-addition salt provides an excess of acid relative to the molar amount of 4-fluorophenylhydrazine. The speed of the Fischer-Indole cyclization can be further influenced by the molar excess of acid relative to 4-fluorophenylhydrazine. When a combination of an acid-addition salt of 4-fluorophenylhydrazine and a second, weaker acid is used, e.g. 4-fluorophenylhydrazine hydrochloride and $NH_4Cl$, $NH_4HSO_4$ or $(NH_4)_2SO_4$, the second, weak acid may for instance be used in amounts of 0.5 to 2, preferable 0.5 to 1.5 molar equivalents relative to the amount of 4-fluorophenylhydrazine. For instance, in one embodiment of the present invention, the acid-addition salt 4-fluorophenylhydrazine hydrochloride is used in combination with an additional amount of $NH_4Cl$. Especially, the second acid $NH_4Cl$ may be present in an amount of 0.5 to 1.5, preferably 1, molar equivalent relative to the amount of 4-fluorophenylhydrazine.

In yet another embodiment of the invention, the activation reagent is a catalytic amount of a heterogeneous Brønsted acid catalyst. In further embodiments of the inventive process, the activation reagent is a catalytic amount of a heterogeneous Brønsted acid catalyst selected from the group consisting of Amberlyst-15, Amberlite-120, Indion-130, Montmorillonite K10 and Zeolite HY, and is preferably selected from Montmorillonite K10 and Amberlyst-15.

In some embodiments of the process according to the invention, the aprotic organic solvent used in the reaction medium is selected from the group consisting of isopropyl acetate and 2-methyltetrahydrofuran or a mixture of the two, and preferable is 2-methyltetrahydrofuran. It was found that when using 2-methyltetrahydrofuran in the reaction medium, the reaction proceeded selectively to yield a crude product of sufficient purity, enabling facile purification and isolation of the product.

In further embodiments of the process according to the present invention, water and the aprotic organic solvent are present in the reaction medium in a volume ratio of from about 1:3 to about 3:1, preferably about 2:3 to about 3:2. Again it was found that especially within these boundaries, the reaction yields 5-fluorotryptophol with high selectivity.

In yet further embodiments of the process according to the present invention, the reaction in step (b) is carried out at a temperature of at least 50° C., more preferably of at least 55° C., most preferably of at least about 60° C. It has been found that at reaction temperatures of about at least 60° C., the solubility of the 4-fluorophenylhydrazine or salts thereof in the reaction medium is significantly increased, which together with the elevated temperature allows a swift and controlled reaction. Consequently, in preferred embodiments of the invention, the reaction temperature is in the range of 60° to 80°, especially of 65° to 75°. In a preferred embodiment, the reaction temperature is about 70° C.

The speed at which the 2,3-dihydrofuran is added to the heterogeneous reaction mixture is not critical. It should be added at a speed that allows a controlled reaction and minimizes the overall reaction time required to complete the reaction. Usually, the addition time will be selected to be in the range from about 15 minutes to about 2 hours, and is often selected to be 1 hour.

The reaction can be carried out either at ambient pressure or under elevated pressure using a reaction vessel suitable for use at such elevated pressures It has furthermore been found that the time required for the phase separation steps (c) and/or (e) can be significantly reduced if these steps are carried out at elevated temperatures. Consequently, in a yet other embodiments of the process of the invention, the phase separation step (c) and/or phase separation step (e) are/is carried out at elevated temperatures, preferably at a temperature in the range of about 40 to 60° C.

Similarly, it has been found that the efficiency of the washing step (d) can be increased if this step is also carried out at elevated temperatures. Consequently, in another embodiment of the process according to the present invention, washing step (d) is carried out at elevated temperatures, preferably in the range between about 40 to 60° C., preferably using an aqueous solution of NaCl.

In a further embodiment of the process according to the invention, all washing and phase separation steps are carried out at an elevated temperature in the range of about 40 to 60° C.

In yet a further embodiment of the process according to the present invention, isolation step (f) comprises the steps of
(f.1.) removal of the aprotic organic solvent from the organic phase obtained in step (e);
(f.2.) adding to the residue obtained in step (f.1.) water or an aqueous solution of at least one inorganic salt and an organic solvent having a water solubility at 20° C. below 5 g/l to form a heterogeneous mixture comprising an aqueous and an organic phase;
(f.3.) separating the organic phase from the heterogeneous mixture obtained in step (f.2.);
(f.4.) precipitating the 5-fluorotryptophol from the organic phase obtained in step (f.3.).

It should be clear that for the separation of the organic phase from the heterogeneous mixture obtained in step (f.2.), phase separation of the aqueous and the organic phase of said mixture must take place, i.e. the heterogeneous mixture must not form a stable emulsion, otherwise isolation of the organic phase and removal of the aqueous phase would not be possible.

The aprotic organic solvent in step (f.1.) can for instance be removed by evaporation, especially at reduced pressure and/or elevated temperature. To facilitate precipitation/crystallization of the 5-fluorotryptophol from the organic phase, part of the organic solvent can be removed via evaporation and/or the solution of 5-fluorotryptophol in said organic solvent can be cooled, e.g. to temperatures below about 10° C., e.g. about 6° C. or lower.

In further embodiments of the inventive process, the organic solvent added in step (f.2.) is toluene or benzene, preferably toluene.

Furthermore, in yet further embodiments of the process according to the invention the formation of the heterogeneous mixture in step (f.2.) and/or the separation of phases in step (f.3.) is/are carried out at elevated temperatures, preferably at a temperature in the range from about 40 to 60° C.

In yet a further embodiment of the process according to the present invention, the process comprises the steps of
a.) forming mixture comprising 4-fluorophenylhydrazine, at least one protic organic or inorganic acid in an amount at least equimolar relative to the 4-fluorophenylhydrazine, water and at least one aprotic organic solvent selected from the group consisting of tetrahydrofuran, 2-methyltetrahydrofuran, and isopropyl acetate, wherein water and the aprotic organic solvent are present in the reaction medium in a volume ratio of from about 1:3 to about 3:1, preferably about 2:3 to about 3:2;

b) adding at a temperature of at least 50° C., preferably at least 60° C., to the mixture a solution of about 0.9 to 1.1 equivalent relative to the amount of 4-fluorophenylhydrazine of 2,3-dihydrofuran in at least one aprotic organic solvent selected from the group consisting of tetrahydrofuran, 2-methyltetrahydrofuran and isopropyl acetate, to react with the 4-fluorophenylhydrazine to give 5-fluorotryptophol, wherein the aprotic solvent and water provided in steps a) and b) are provided in a ratio relative to each other such that a heterogeneous reaction mixture comprising a liquid organic and a liquid aqueous phase is formed either before or during addition step b);

c) separating the liquid organic from the liquid aqueous phase;

d) contacting at an elevated temperature in the range of about 40 to about 60° C. the liquid organic phase with an aqueous solution of at least one inorganic salt to form a heterogeneous mixture comprising an organic liquid phase and an aqueous liquid phase;

e) separating the heterogeneous mixture into the liquid organic and the liquid aqueous phase and isolating the liquid organic phase;

f.1.) removing the aprotic organic solvent from the organic phase obtained in step (e);

f.2.) adding to the residue obtained in step (f.1.) water or an aqueous solution of at least one inorganic salt and an organic solvent having a water solubility at 20° C. below 5 g/l to form a heterogeneous mixture comprising a liquid aqueous and a liquid organic phase;

f.3.) separating the organic phase from the heterogeneous mixture obtained in step (f.2.);

f.4.) precipitating the 5-fluorotryptophol from the organic phase obtained in step (f.3.).

Again, is should be clear, that in order to separate the liquid organic phase from the heterogeneous mixture, phase separation of the mixture into its aqueous and organic phase must take place, i.e. the mixture must not be a stable emulsion of the two phases.

Preferably, the organic solvent added in step (f.2.) is selected from toluene and benzene and preferably is toluene.

Preferably, the activation agent is selected from the group of organic and inorganic protic acids consisting of $H_2SO_4$, HCl, $NH_4HSO_4$, $(NH_4)_2SO_4$, acetic acid, $NH_4Cl$, $H_3PO_4$, $(NH_4)H_2PO_4$, $HClO_4$ or $(NH_4)ClO_4$, or mixtures thereof especially from the group consisting of $H_2SO_4$ and HCl or mixtures thereof. Preferably, the protic acid is present in an excess relative to the amount of 4-fluorophenylhydrazine used in the reaction.

Preferably, the aprotic organic solvent used in step a) is 2-methyltetrahydrofuran or isopropylacetate, or a mixture of said two solvents.

Preferably, the mixture formed in step a) is a heterogeneous mixture comprising a liquid organic phase and a liquid aqueous phase.

Preferably, in step a) relative to the 4-fluorophenylhydrazine at least one equivalent of a first acid selected from the group consisting of HCl, HBr, $H_2SO_4$, $H_3PO_4$ and $HClO_4$ and an additional amount of a second acid selected from the group consisting of $NH_4Cl$, $NH_4HSO4$, $(NH_4)_2SO_4$, $(NH_4)H_2PO_4$, $(NH_4)2HPO_4$, and $(NH_4)_3PO_4$ are used as the activation reagent. Preferably, the first acid is selected from HCl and $H_2SO_4$ and the second acid is selected from $NH_4Cl$ or $(NH_4)_2SO_4$. The second acid may for instance be used in amounts of 0.5 to 2, preferable 0.5 to 1.5 molar equivalents relative to the amount of 4-fluorophenylhydrazine. In some embodiments of the present invention, the second acid is used in an equimolar amount relative to 4-fluorophenylhydrazine. For instance, in one embodiment of the present invention, the acid-addition salt 4-fluorophenylhydrazine hydrochloride is used in combination with an additional amount of $NH_4Cl$. Especially, the second acid $NH_4Cl$ may be present in an amount of 0.5 to 1.5, preferably 1, molar equivalent relative to the amount of 4-fluorophenylhydrazine. Preferably, all washing and phase separation steps in the process according to the invention are carried out at an elevated temperature, especially at a temperature in the range of about 40° C. to 60° C.

In a further aspect of the invention, a process for the preparation of a compound according to formula (I) is provided, optionally in the form of a physiologically acceptable acid addition salt thereof,

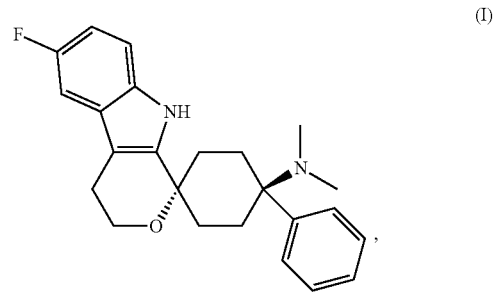 [SMILES: CN(C)[C@]1(c2ccccc2)CC[C@]2(CC1)OCCc1c3cc(F)ccc3[nH]c12]

(I)

comprising the steps of
(a) providing 5-fluorotryptophol by the above described inventive process and
(b) reacting the 5-fluorotryptophol in an acid-catalysed Oxa-Pictet-Spengler reaction with a compound according to formula (II), in each case optionally in the form of an acid addition salt,

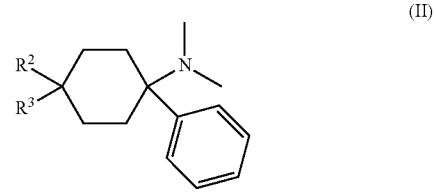

(II)

wherein radicals $R^2$ and $R^3$ of the compound according to formula (II) together denote =O, or together with the carbon atom connecting them form a cyclic moiety selected from the group consisting of

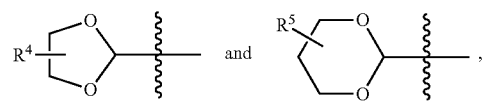

wherein $R^4$ and $R^5$ independently of one another represent in each case 0, 1, 2, 3 or 4 substituents selected from the group consisting of H and $CH_3$, to form a compound according to formula (I).

FIGURES

FIGS. 1a to 1c show the 1H-NMR spectra of Samples 1 to 3 described in Example 3 below.

EXAMPLES

The following examples further illustrate the invention but are not to be construed as limiting its scope.
Abbreviations:
DMAC: Dimethylacetamid
THF: Tetrahydrofuran
RT: Reaction temperature
n.d.: Not determined
$T_a$: Temperature at addition of 2,3-dihydrotetrafuran
$t_{ad}$: Addition time of 2,3-dihydrotetrafuran
$t_{rct}$: Reaction time after addition of 2,3-dihydrotetrafuran
DMF: Dimethylformamide
MTBE: methyl tert-butyl ether
2-MeTHF: 2-methyltetrahydrofuran

Comparative Example 1

The following reaction procedure was developed based on the procedure described in K. R. Campos et al, *Org. Lett.*, Vol 6, No. 1, 2004, 79-82 (see above).

30 g of 4-fluorophenylhydrazine hydrochloride (185 mmol) were suspended in 150 ml dimethylacetamide (DMAC) and 300 ml $H_2SO_4$ (4%, aqueous). The suspension was heated up to 75 to 80° C. whilst stirring, whereby the hydrazine dissolved. A solution of 12.9 g of 2,3-dihydrofuran (185 mmol) in 150 ml DMAC was added dropwise to the reaction mixture over a period of 30 to 60 minutes and the reaction mixture was stirred for 2 h at 80 to 85° C. Then, the reaction mixture was cooled to ambient temperature and 600 ml ethyl acetate were added. After 5 to 10 minutes of vigorous stirring, the phases were separated using a separation funnel. The organic phase was isolated and washed 4 times using 250 ml of an aqueous sodium chloride (5%) solution, respectively. The organic solvent was removed from the washed organic phase via evaporation at reduced pressure and at elevated temperature (45-60° C., 160-9 mbar). The residue was dissolved at 20 to 25° C. in about 4 times its weight in toluene and the solution was stirred for 1 h at ambient temperature. If crystallization had not yet set in, seed crystals were added to the solution. The solution was cooled to 0-3° C. and kept at this temperature for 2 to 3 h whilst continuing to stir the solution. The precipitated crystals were isolated via filtration and washed with 10-20 ml of cold toluene (0-3° C.). The isolated solid was dried at 45° C. at reduced pressure (50-60 mbar) and the product was obtained in about 25% yield as wax-like, nearly white crystals with a melting point of 60±1° C.

Although this procedure yields 5-fluorotryptophol in a sufficient purity to allow purification and isolation of the product via crystallization, the product is obtained only in a relatively low yield. Additionally, it is necessary to wash the organic phase four times with water to remove the DMAC. Without this repeated washing procedure, it was not possible to crystallize the product.

Comparative Example 2

Based on the procedure described as comparative example 1 above, it was tried to adapt the procedure based on the disclosure in Y. Lü et al, Journal of Chemical Engineering of Chinese Universities, No. 1, Vol. 24, 2010, p 127 to 131 (see above), i.e. by using a heterogeneous solvent mixture of water/ethanol/toluene instead of a homogeneous solvent mixture of water and DMAC.

5 g 4-fluorophenylhydrazine hydrochloride (30.75 mmol), together with 3.5 g ammonium chloride (65.43 mmol) were mixed with 12.5 ml toluene, 12.5 ml ethanol and 46.5 ml of water. The mixture was heated to 70° C. and a second mixture consisting of 2.16 g of 2.3 dihydrofuran (30.75 mmol) in 12 ml toluene and 12 ml ethanol was added dropwise at this temperature over a period of 30 minutes whilst continuously stirring. The reaction mixture was kept at 70° C. overnight whilst stirring and after 17 h cooled down to 55° C. A solution of 5%-NaCl in water (33.75 ml) was added and the mixture was heated to 55° C. whilst vigorously stirring. The organic and aqueous phase were left to separate at 50° C. The organic phase was isolated and the solvent removed at reduced pressure (<10 mbar) and at elevated temperature (65° C.). A sample of the raw product was taken and the content of 5-fluorotryptophol and several by-products, including "side-product A" (see below) was determined via HPLC-analysis. It was tried to crystallize 5-fluorotryptophol from a solution of the raw-product in toluene, but without success.

The experiment was repeated analogously using mixtures of toluene and ethanol in a volume ratio of 5:1 and 1:5 as the organic solvent for the Fischer-Indole cyclization reaction. In none of the experiments, was it possible to crystallize 5-fluorotryptophol from a solution of the raw product in toluene. Without wanting to be bound by theory, it is believed that this is due to the high amount of by-products formed in the reaction, which are difficult to separate from the product without using chromatography. One such by-product is for instance the following compound which will be referred to in the following as "by-product A"

„by-product A":

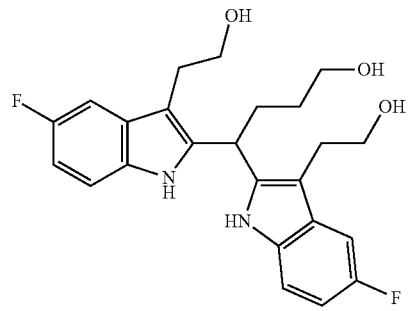

Table 1 list the respective purity/content of 5-fluorotryptophol and "side product A" as determined in the raw product.

TABLE 1

| Organic solvent | Product purity* | By-product A** |
|---|---|---|
| Toluene/EtOH 1:1 (12.5 ml:12.5 ml) | 85.7% | 11.1% |
| Toluene/EtOH ≈ 5:1 (20.75 ml:4.25 ml) | 85.2% | 9.1% |
| Toluene/EtOH ≈ 1:5 (4.25 ml:20.75 ml) | 81.0% | 13.1% |

*Purity according to HPLC
**According to HPLC.

Comparative Example 3

The procedure according to comparative example was repeated analogously but substituting DMAC by different organic solvents. Additional changes to the general procedure are listed under the heading comments below in Table 2 together with the analytical results:

TABLE 2

| Solvent | Comment | Product content* (raw product) | by-product A** (raw product) |
|---|---|---|---|
| n-propanol | RT = 85° C.; product isolated via chromatography. | 49.3% | n.d. |
| n-propanol | RT = 85° C.; product isolated via chromatography | 67.4% | n.d. |
| n-propanol | $T_a$ = 52° C.; RT = 87° C.; product did not crystallize | 67.4% | 21% |
| i-propanol | $t_{ad}$ = 60 min; RT = 80° C.; product did not crystallize | 67.3% | 29% |
| Ethanol | RT = 75° C.; $t_{ad}$ = 60 min;; product did not crystallize | 61.2% | 33% |
| glacial acetic acid | RT = 80° C.; $t_{ad}$ = 60 min; product did not crystallize | 24.7% | n.d. |
| n-butanol | RT = 80° C.; $t_{ad}$ = 60 min; product did not crystallize | 75.3% | 20.2% |
| Toluene | RT = 80° C.; $t_{ad}$ = 60 min; product did not crystallize | 44.7% | 39.4% |
| DMF | RT = 80° C.; $t_{ad}$ = 60 min; product did not crystallize | 48.5% | 0.4% |
| n-butylacetate | RT = 68° C.; $t_{ad}$ = 20 min; product did not crystallize | 91% | 1.6% |
| i-butyl acetate | RT = 67° C.; $t_{ad}$ = 18 min; product did not crystallize | 89.5% | 2.5% |
| t-BME | RT = 55° C.; $t_{ad}$ = 30 min; product did not crystallize | 83.1% | 1.75% |
| dichloroethane | RT = 70° C., $t_{ad}$ = 60 min; product formed a slimy phase even before work up | 77.6% | 19.1% |

*Purity according to HPLC,
**According to HPLC

Example 1

The following reaction procedure was carried out under an $N_2$-atmosphere due to general laboratory safety considerations. 500 g of 4-fluorophenylhydrazine hydrochloride (3.08 mol) were suspended in a mixture of 2.5 l of 2-methyltetrahydrofuran and an aqueous solution of ammonium chloride [350 g ammonium chloride (6.54 mol) in 4650 ml of water]. The suspension was heated to 70° C. whereby the 4-fluorophenylhydrazine was completely dissolved in the heterogeneous reaction medium formed by the aqueous solution and the organic solvent. Over a period of 1 h, 215.5 g 2,3-dihydrofuran (3.08 mol) dissolved in 2.4 l 2-methyltetrahydrofuran were added to the heterogeneous reaction medium whilst stirring and after completion of the addition, the reaction mixture was stirred at 70° C. for an additional 16 to 24 h. The mixture was then cooled to 50° C., and after 15 minutes without stirring to allow phase separation, the organic and aqueous phase were isolated whilst maintaining the temperature at 50° C. To the organic phase a washing solution consisting of 180 g sodium chloride dissolved in 3375 ml of water was added and the mixture was stirred vigorously for 10 minutes at 50° C. Stirring was stopped and the organic phase was allowed to separate from the aqueous phase during 15 minutes and was then isolated, all of which was done whilst maintaining the temperature at 50° C. The organic solvent was removed from the organic phase at 55° C. under reduced pressure (<10 mbar). The resulting residue was extracted with a mixture of toluene (4050 ml) and water (1250 ml) at a temperature of 50° C., the organic phase was isolated whilst being maintained at 50° C. and 1400 ml of the toluene comprised in said phase were removed via evaporation at a temperature of not more than 65° C. and at reduced pressure (150 mbar). Whilst continuing to stir, the remaining organic solution was carefully cooled to 5° C. to precipitate 5-fluorotryptophol in crystalline form. At a temperature of 10-15° C. seed crystals were added to the solution. The solution was maintained at 5° C. for an additional 16 to 24 h whilst stirring. Then the precipitate was isolated via filtration and washed several times with cooled toluene (+3° C., in total 500 ml). The resulting solid was dried overnight at 35° C. in a drying cabinet providing 5-fluorotryptophol as a yellow to white solid (m.p. 62° C.; purity (HPLC)>98%) in about 65% yield.

The following solvents were also tested for purification/isolation via precipitation of crystalline product from respective solutions of raw product obtained according to the above procedure: Heptane, cyclohexane, diethyl ether, diisopropyl ether, methyl tert-butyl ether, acetone, methyl ethyl ketone, ethyl acetate, methanol, ethanol, isopropanol and benzene. Additionally, the following mixtures were tested: ethyl acetate:heptane (1:1); isopropanol:heptane (1:1); and acetone:heptane (1:1).

Except for benzene, none of these solvents or solvent mixtures was found to be suitable for the purification step via precipitation/crystallization as described above in connection with toluene.

Example 2

The following reaction was carried out under an $N_2$-atmosphere due to general laboratory safety considerations. 12 g 4-fluorophenylhydrazine hydrochloride (73.81 mmol) were suspended in a mixture of 30 ml isopropylacetate and 30 ml 2-methyltetrahydrofuran and an aqueous solution of ammonium chloride [8.4 g ammonium chloride (157 mmol) in 111.6 ml of water]. The suspension was heated to 70° C.

Over a period of 25 min, 5.17 g 2,3-dihydrofuran (73.8 mmol) dissolved in 28.8 ml 2-methyltetrahydrofuran were added to the heterogeneous reaction medium whilst stirring. After completion of the addition, the reaction mixture was stirred at 70° C. for additional 16 h. The mixture was then cooled to 55-50° C. and stirring was ceased. 15 minutes after the stirring was stopped the organic and aqueous phase were separated whilst maintaining the temperature at 50° C. A washing solution consisting of 4.32 g sodium chloride dissolved in 81 ml of water was added to the organic phase and the mixture was stirred vigorously for 10 minutes at 50° C. Stirring was stopped and the organic phase was allowed to separate from the aqueous phase during 15 minutes and then isolated, all of which was done whilst maintaining the temperature at 50° C. The organic solvent was removed from the organic phase at 55° C. under reduced pressure (<50 mbar). The resulting residue was extracted with a mixture of toluene (40.5 ml) and water (12.5 ml) at a temperature of 50° C. and the organic phase was isolated whilst being maintained at 50° C. 10 ml of the toluene comprised in said phase were subsequently removed via evaporation at an elevated temperature and at reduced pressure. Whilst continuing to stir, the remaining organic solution was cooled to about 5° C. to precipitate 5-fluorotryptophol in crystalline form. To aid precipitation, seed crystals were added to the solution. The solution was maintained at about 5° C. overnight whilst stirring. Then the precipitate was isolated via filtration and washed several times with cooled toluene (+3° C., a total of 12 ml). The resulting solid was dried overnight at 45° C. in a drying cabinet and provided crystalline 5-fluorotryptophol in about 42.3% yield (5.6 g) and a purity (HPLC) of 98.56%.

Example 3

The following reaction was carried out under an $N_2$-atmosphere due to general laboratory safety considerations. 5 g 4-fluorophenylhydrazine hydrochloride (30.75 mmol) was suspended in a mixture of 25 ml 2-methyltetrahydrofuran and an aqueous solution of ammonium chloride (3.5 g ammonium chloride (65.4 mmol) in 46.5 ml of water). The suspension was heated to 70° C. Over a period of 12 min, 2.15 g 2,3-dihydrofuran (30.75 mmol) dissolved in 24 ml 2-methyltetrahydrofuran were added to the heterogeneous reaction medium whilst stirring. After completion of the addition, the reaction mixture was stirred at 70° C. for additional 16 h. The mixture was then cooled to 55° C. and stirring was ceased. 15 minutes after the stirring was stopped the organic and aqueous phase were separated whilst maintaining the temperature at 55° C. A sample of the aqueous phase was taken for NMR-analysis (Sample 1). A washing solution consisting of 1.8 g sodium chloride dissolved in 33.7 ml of water was added to the organic phase and the mixture was stirred vigorously for 10 minutes at 55° C. Stirring was stopped and the organic phase was allowed to separate from the aqueous phase during 15 minutes. Again, a sample of the aqueous phase is taken for NMR-analysis (Sample 2). The organic phase was then isolated, all of which was done whilst maintaining the temperature at 55° C. The organic solvent was removed from the organic phase at 55° C. under reduced pressure (<50 mbar). The resulting residue was extracted with a mixture of toluene (40.5 ml) and water (12.5 ml) at a temperature of 50° C. Again a sample of the aqueous phase was taken for NMR-analysis (Sample 3) and subsequently the organic phase was isolated whilst being maintained at 50° C. The solvent was removed from the organic phase yielding a residue of raw product ready for subsequent crystallization. A sample of the residue was taken to analyze its HPLC-purity. The raw product had a HPLC-purity of 94.4%, demonstrating that the process had proceeded in a representative manner.

The NMR-spectra of the different samples taken during the synthesis are shown in FIG. 1. The $^1$H-NMR spectra obtained from these samples demonstrate that, surprisingly, in Samples 1 and 2 essentially no product is found. This becomes apparent from the lack of $^1$H-peaks characteristic for 5-fluorotryptophol. In the spectra of Samples 1 and 2 the only signals found in the area typical for protons bound to aromatic cycles are signals which can be assigned to unreacted 4-fluorophenylhydrazine. The NMR-spectra of Sample 2 also shows that the washing step with the aqueous sodium chloride solution selectively removes not only 4-fluorophenylhydrazine from the organic phase but also other organic by-products. $^1$H-NMR peaks assignable to the product are for the first time found in the spectrum obtained from Sample 3, which was taken at a stage in the process in which 2-methyltetrahydrofuran had been removed and substituted by toluene. Consequently, the use of the solvent 2-methyltetrahydrofuran enables the efficient isolation and purification of 5-fluorotryptophol from the reaction mixture.

Example 4 a) The reaction as described in Example 1 was run analogously on a smaller scale, except for using 1.15 equivalent of 2,3-tetrahydrofuran (2.48 g; 35.37 mmol) instead of equimolar amounts. This resulted in a significant drop in the overall yield of the product to 30.8%, which was isolated as an orange/brown, sticky solid and after drying overnight at 40° C. under reduced pressure (75-150 mbar) had molten. This is considered to be indicative of the presence of significant amounts of by-products/impurities in the product. This was confirmed by measurement of the HPLC-purity of the material, which was found to be only at 93.46%.

b) The reaction as described in Example 1 was run analogously on a smaller scale, except for using 0.95 equivalents of 2,3-tetrahydrofuran (4.38 g, 62.51 mmol) instead of equimolar amounts. This variation produced product in a satisfactory yield (55%) and of satisfactory purity (98.7%).

Example 5

The reaction as described in Example 1 was run analogously on a smaller scale (30.72 mmol 4-fluorophenylhydrazine), with the exception that in a first experiment the ratio of water to 2-methyltetrahydrofuran present in the heterogeneous reaction medium after addition of the 2,3-dihydrotetrafuran was about 1:3 (24.5 ml 2-MeTHF/71.5 ml $H_2O$; Example 5.1.), in a second experiment was about 1:5 (16.5 ml 2-MeTHF/81.5 ml $H_2O$; Example 5.2), and in a third experiment was about 5:1 (83 ml 2-MeTHF/15 ml $H_2O$; Example 5.3). [Instead of using 2-MeTHF and water in the ratio of about 1:1 as described in Example 1 (4.9 1 2-MeTHF: 4.65 1$H_2O$)].

In the first experiment (Ex. 5.1.) the overall yield of product was significantly reduced (25.4%) and again, the solid obtained via crystallization did melt when dried overnight at 40° C. at reduced pressure. HPLC-purity of the product was found to be 93.49%.

In the second experiment (Ex. 5.2.) the phase separation after the cyclization reaction was incomplete and the experiment was therefore terminated at this stage.

In the third experiment (Ex. 5.3.) the amount of water was insufficient to dissolve all of the ammonium chloride in the reaction medium, which made the phase separation after the cyclization reaction difficult. Extraction with toluene was not possible because the raw product obtained at that stage of the reaction (containing according to HPLC-purity analysis about 3% of by-product A) did not dissolve in toluene. The experiment was therefore terminated at this stage.

Example 6

The following reaction was carried out under an $N_2$-atmosphere due to general laboratory safety considerations. 11.27 g 4-fluorophenylhydrazine hydrochloride (69.32 mmol) was suspended in a mixture of 56 ml tetrahydrofuran 113 ml of aqueous sulfuric acid (4%) and the mixture was heated to 63° C., thereby forming an orange solution. Over a period of 66 min and at a temperature of 63 to 65° C. 4.85 g 2,3-dihydrofuran (69.32 mmol) dissolved in 56 ml tetrahydrofuran was added to the solution whilst stirring. During the course of the addition the solution became first opaque then formed a heterogeneous two phase system, comprising a liquid organic phase and a liquid aqueous phase. The heterogeneous reaction medium was stirred for an additional 2 h at 65° C. then cooled to 10° C. The cooled heterogeneous reaction medium was extracted with 225 ml isopropylacetate and the resulting organic phase was separated from the aqueous phase and washed two times with 90 ml of demineralized water. The organic solvent was removed via evaporation at reduced pressure (<1 mbar) at 45° C. The residue thus obtained was weighed (10.2 g) and 2.6 times its weight of toluene were added. The resulting solution was stirred for about 16 h at 5-8° C., wherein seed crystals were added to the solution after two hours of stirring. The precipitated solid was isolated via filtration and washed two times with 8 to 10 ml of cooled toluene (5-8° C.). The resulting solid was dried at 45° C. at reduced pressure (75-100 mbar) for 22 h, yielding 3.0 g of product (25% yield) with a HPLC-purity of 99.67%.

Example 7

The following reaction was carried out under an $N_2$-atmosphere due to general laboratory safety considerations. 20 g 4-fluorophenylhydrazine hydrochloride (123 mmol) was suspended in a mixture of 100 ml tetrahydrofuran and an aqueous solution of 14 g $NH_4Cl$ in 186 ml of water. The mixture was heated to 65° C. At this temperature not all of the hydrazine hydrochloride was dissolved and the mixture formed a heterogeneous system, part of the THF in the mixture forming a liquid organic phase. Over a period of 50 min and at a temperature of 65° C. 8.6 g 2,3-dihydrofuran (123 mmol) dissolved in 96 ml tetrahydrofuran was added to the heterogeneous reaction medium whilst stirring. The heterogeneous reaction medium was stirred for an additional 16 h at 70° C. then cooled to 50° C. At this temperature, the organic phase was separated from the aqueous phase. An aqueous solution of sodium chloride (7.2 g NaCl in 135 ml of water) was added to the organic phase and the mixture was vigorously stirred for 15 min at 50° C. Stirring was stopped and after 10 minutes the organic phase was separated from the organic phase. The organic solvent was removed from the organic phase via evaporation at 45° C. at reduced pressure (<10 mbar). To the thus obtained residue 160 ml of toluene and 50 ml of water were added and the resulting mixture was vigorously stirred for 10 minutes. After the stirring was stopped the mixture formed a three-phase system. The solid phase was isolated and the remaining two liquid phases were left to separate for another 12 minutes. The organic phase was isolated and 56 ml of toluene were removed via evaporation (55° C./90 mbar) to be replaced by 56 ml of toluene. Again 56 ml of toluene were removed via evaporation (55° C./90 mbar). The resulting solution was then cooled to 5° C., seed crystals were added and the solution then stirred at 5-8° C. for about 16 h. The precipitated solid was isolated via filtration and washed with little toluene. The solid was dried for two days at 30° C. and reduced pressure (75-100 mbar), yielding 7.8 g (35.4%) of yellow product with a HPLC-purity of 98.76%.

Example 8

To test the use of different aprotic acids, the process as described in Example 2 was conducted using the reagents as described below in table 3. The amounts of reagents and solvents were calculated based on an amount of 11.27 g of 4-fluorophenylhydrazine hydrochloride (69.3 mmol). Deviations from the procedure described in Example 2 are indicated in the table.

TABLE 3

| Example | Protic acid/ Second protic acid | $t_{ad.}$ | $t_{rct.}$ | Washing solution | Yield | Assay | Comment |
| --- | --- | --- | --- | --- | --- | --- | --- |
| 7.1 | 1% aq. $H_2SO_4$ | 1 h | 2.5 | h20% aq. NaCl/0.2% aq. $H_2SO_4$ (twice) | 36% | 100.5 % | The toluene solution is dried using $Na_2SO_4$ |
| 7.2 | 2% aq. $H_2SO_4$ | 1 h | 2.5 | h20% aq. NaCl/0.2% aq. $H_2SO_4$ (twice) | 51% | 99.8 % | The toluene solution is dried using $Na_2SO_4$ |
| 7.3 | 4% aq. $H_2SO_4$ | 1 h | 2.5 | h20% aq. NaCl/0.2% aq. $H_2SO_4$ (twice) | 52% | 100.4 % | The toluene solution is dried using $Na_2SO_4$ |
| 7.4 | 8% aq. $H_2SO_4$ | 1 h | 2.5 | h10 % aq. NaCl (twice) | 27% | 98.7 % | RT = 50° C., the toluene solution is dried using $Na_2SO_4$ |
| 7.5 | 8% aq. $NH_4HSO_4$ | 1 h | 3 | h10 % aq. NaCl (twice) | 49% | 100.6 % | The toluene solution is dried using $Na_2SO_4$ |
| 7.6 | 5% aq. $(NH_4)HSO_4$/ 10% aq. $(NH_4)_2SO_4$ | 1 h | 71 | h10 % aq. NaCl (twice) | 50% | 96.4 % | The toluene solution is dried using $Na_2SO_4$ |
| 7.7 | 5% aq. $(NH_4)HSO_4$/ 10% aq.$(NH_4)_2SO_4$ | 1 h | 21.5 | h10 % aq. NaCl (twice) | 66% | 94.9 % | The toluene solution is dried using $Na_2SO_4$ |

Example 9

In this example it was demonstrated that addition salts other then 4-fluorophenylhydrazine hydrochloride can be used in the process according to the invention:

220 g of 4-fluorophenylhydrazine hydrochloride were provided together with 1100 ml 2-MeTHF and 440 ml H$_2$O. To liberate the hydrazine, 32% aq. NaOH was added whilst cooling. After the neutralization reaction, the organic phase containing the 4-fluorophenylhydrazine was separated from the aqueous phase. Subsequently, 94.84 g of 2,3-dihydrofurane were added to the isolated organic phase and the resulting mixture was slowly (5.5 h) added to a solution of 440 g NH$_4$HSO$_4$ in 2046 ml water and 1056 ml 2-MeTHF, which has been heated to 70° C. The reaction was kept at this temperature for an additional 16.5 h whilst stirring.

The reaction mixture was cooled to 53° C. and the phases were allowed to separate. The aqueous phase was then removed and sodium chloride solution (79.2 g NaCl in 1485 ml water) was added. The resulting mixture was vigorously stirred at a temperature of 50° C., then the phases were again allowed to separate and the aqueous phase was removed. The solvent was removed from the remaining organic phase via evaporation at 55° C. and reduced pressure (<10 mbar). 1782 ml of toluene and 550 ml of water were added at 55° C. to dissolve the residue. After phase separation 650 ml of toluene were removed via evaporation at 65° C. and reduced pressure (150 mbar). The remaining solution was cooled to below 6° C., seed crystals were added, and 5-fluorotryptophol was precipitated from the solution. The product was isolated via filtration and washed several times with small quantities of cold toluene. The remaining crystalline solid was dried overnight at 45° C. and at reduced pressure in a drying cabinet. 5-fluorotryptophol was obtained in a yield of 58%. The product had a HPLC-purity of 99.5%.

Example 10

In this example commercially available montmorillonite K10 was used as a heterogeneous Brønsted acid catalyst.

10 g (61.5 mmol) of 4-fluorophenylhydrazine hydrochloride were suspended in 50 ml of 2-methyltetrahydrofurane. A suspension of montmorillonite K10 (7 g) in 93 ml of water were added to this suspension. The mixture was heated to 72° C. whilst being vigorously stirred. Subsequently, over a period of 50 minutes a solution of 4.3 g (61.5 mmol) of 2,3-dihydrofurane in 50 ml of 2-methyltetrahydrofurane was added to the mixture. The reaction mixture was maintained at 72° C. overnight (approx. 16 h) whilst continuing to stir. Then the insoluble components of the mixture were removed via filtration through a glass fritt (pore size 3). The organic and the aqueous phase were separated from one another and the isolated organic phase was washed by adding a solution of 3.6 g sodium chlorid in 68 ml of water and stirring the mixture at 50° C. for 10 minutes. Again the organic and the aqueous phase were separated from each other and solvent was removed from the organic phase at 60° C. and a reduced pressure of <10 mbar. To the residue 80 ml of toluene and 25 ml of water were added and the mixture was stirred for 10 minutes at 50° C. The aqueous phase and the organic phase were again separated from each other and the organic solvent was removed from the organic phase at reduced pressure (<10 mbar) and at 60° C. The residue was dissolved in 28 ml of toluene and cooled overnight to 5-8° C. To facilitate crystallization seed crystals of 5-fluorotryptophole were added. The precipitate was filtered off and dried for 2 days at 40° C. and at a reduced pressure of 75 to 100 mbar. 5-fluorotryptophole was obtained 6.2 g (56%)/99.5% purity (HPLC).

The invention claimed is:

1. A process for preparing 5-fluorotryptophol comprising steps of
    a) providing a mixture comprising 4-fluorophenyl-hydrazine, an activation reagent, water and at least one aprotic organic solvent selected from the group consisting of tetrahydrofuran, 2-methyltetrahydrofuran and isopropyl acetate;
    b) adding to the mixture a solution of at the most about 1.1 equivalents of 2,3-dihydrofuran in at least one aprotic organic solvent selected from the group consisting of tetrahydrofuran, 2-methyltetrahydrofuran and isopropyl acetate to react with the 4-fluorophenylhydrazine to give 5-fluorotryptophol, wherein the aprotic solvent and water provided in steps a) and b) are provided in a ratio relative to each other such that a heterogeneous reaction mixture comprising a liquid organic phase and a liquid aqueous phase is formed either before or during addition step b);
    c) separating the organic from the aqueous phase;
    d) contacting the organic phase with an aqueous solution of at least one inorganic salt to form a heterogeneous mixture comprising a liquid organic phase and a liquid aqueous phase;
    e) separating the organic phase from the aqueous phase of the heterogeneous mixture; and
    f) isolating 5-fluorotryptophol from the organic phase via a precipitation step.

2. The process according to claim 1, wherein the mixture formed in step a) is a heterogeneous mixture comprising a liquid organic phase and a liquid aqueous phase.

3. The process according to claim 1, wherein the activation reagent is at least one protic acid or a heterogeneous Bronsted acid catalyst.

4. The process according to claim 1, wherein the activation reagent is
    a) a protic acid in an amount of at least one equivalent relative to the 4-fluorophenylhydrazine or
    b) a catalytic amount of a heterogeneous Bronsted acid catalyst.

5. The process according to claim 1, wherein the activation reagent is a protic acid that has a pK$_a$-value in the range of −6.5 to +10.

6. The process according to claim 5, wherein the protic acid is added to the reaction medium in the form of its addition salt with 4-fluorophenylhydrazine.

7. The process according to claim 1, wherein the activation reagent is HCl.

8. The process according to claim 1, wherein the activation agent is a mixture of one equivalent relative to 4-fluorophenylhydrazine of an acid selected from the group consisting of HCl, HBr, H$_2$SO$_4$, H$_3$PO$_4$ and HClO$_4$ and an additional amount of a second acid selected from the group consisting of NH$_4$Cl, NH$_4$HSO$_4$, (NH$_4$)$_2$SO$_4$, (NH$_4$)H$_2$PO$_4$, (NH$_4$)$_2$HPO$_4$, and (NH$_4$)$_3$PO$_4$.

9. The process according to claim 8, wherein the second acid is NH$_4$Cl.

10. The process according to claim 1, wherein the activation reagent is a catalytic amount of a heterogeneous Bronsted acid catalyst selected from the group consisting of Amberlyst-15, Amberlite-120, Indion-130, Montmorillonite K10 and Zeolite HY.

11. The process according to claim 1, wherein the aprotic organic solvent is selected from the group consisting of isopropyl acetate and 2-methyltetrahydrofuran or mixtures thereof.

12. The process according to claim 1, wherein water and the aprotic organic solvent are present in the heterogeneous reaction medium at a volume ratio of from about 1:3 to about 3:1.

13. The process according to claim 1, wherein the reaction in step (b) is carried out at a temperature of at least about 50° C.

14. The process according to claim 1, wherein phase separation step (c) is carried out at elevated temperatures in a range between 40° C. to 60° C.

15. The process according to claim 1, wherein the formation of the heterogeneous mixture in step (d) is carried out at elevated temperatures in a range between 40° C. to 60° C.

16. The process according to claim 1, wherein phase separation step (e) is carried out at elevated temperatures in a range between 40° C. to 60° C.

17. The process according to claim 1, wherein isolation step (f) comprises steps of f1) removal of the aprotic organic solvent from the organic phase obtained in step (e) to give a residue;

f2) adding to the residue obtained in step f1) water or an aqueous solution of at least one inorganic salt and an organic solvent having a water solubility at 20° C. below 5 g/l to form a heterogeneous mixture comprising a liquid aqueous phase and a liquid organic phase;

f3) separating the liquid organic phase from the heterogeneous mixture obtained in step f2); and f4) precipitating the 5-fluorotryptophol from the liquid organic phase obtained in step f3).

18. The process according to claim 17, wherein the organic solvent added in step f2) is toluene or benzene.

19. The process according to claim 17, wherein the formation of the heterogeneous mixture in step f2) and/or the separation of the liquid organic phase in step f3) are/is carried out at elevated temperatures in a range from 40° C. to 60° C.

20. The process according to claim 1, wherein in step b) relative to 4-fluorophenylhydrazine about 0.9 to 1.1 equivalent of 2,3-dihydrofuran are added to the heterogeneous reaction mixture.

* * * * *